United States Patent [19]

Kim

[11] Patent Number: 6,054,314

[45] Date of Patent: Apr. 25, 2000

[54] METHOD FOR COLLECTING CELLS FROM INTERNAL ORGANS

[75] Inventor: Nam Woo Kim, San Jose, Calif.

[73] Assignee: Geron Corporation, Menlo Park, Calif.

[21] Appl. No.: 08/926,648

[22] Filed: Sep. 10, 1997

[51] Int. Cl.[7] .............................. C12N 5/06; C12Q 1/68; C12Q 1/34

[52] U.S. Cl. ................................ 435/325; 435/6; 435/15; 435/18; 435/7.1; 435/4; 435/91.2; 435/378; 435/379; 436/63; 601/46; 607/1; 607/61

[58] Field of Search ........................... 435/6, 7.1, 4, 91.2, 435/325, 15, 18, 378, 379; 128/915, 916; 601/46; D24/215; 436/63; 607/1, 61

[56] References Cited

U.S. PATENT DOCUMENTS 5,489,508  2/1996  West et al. .................................. 435/6

OTHER PUBLICATIONS

Lenz et al. Prenatal Diagnosis. 5:259–267, 1985.

*Primary Examiner*—Carla J. Myers
*Attorney, Agent, or Firm*—David J. Earp

[57] ABSTRACT

A substantially non-invasive and efficient method for collecting cells from the internal organs of a subject is provided. In one embodiment, energy from an external energy source is applied to the subject that is sufficient to loosen the cells from an internal cellular surface of an internal organ so that at least a portion of the loosened cells are detached from the internal cellular surface or the organ. The detached cells are collected from the subject and can be analyzed for a disease state. The methods described herein provide methods for detecting of disease states before macroscopic evidence of the disease state that also facilitate inexpensive mass screening.

32 Claims, 1 Drawing Sheet

METHOD FOR COLLECTING CELLS FROM INTERNAL ORGANS

BACKGROUND OF THE INVENTION

1. The Field of the Invention

The instant invention provides methods relating to medical and diagnostic technology. In particular, the present invention provides substantially non-invasive methods for collecting cells from the internal organs of a subject.

2. The Background Art

The diagnosis of many diseases requires an analysis of cells collected from specific internal organs, such as the lungs, kidneys, uterus, or bladder. Often, invasive procedures such as punch biopsies, needle biopsies, cystoscopy, scrapings, and the removal of portions of the internal organ are required to collect the quantities and types of cells necessary for analysis. Such methods are expensive and often cause considerable subject discomfort leading to decreased subject compliance and limiting mass screening for certain disease states, especially cancer.

Bladder carcinoma illustrates the need for a less expensive, more efficient, and substantially non-invasive method for collecting cells for disease analysis. This cancer is associated with cigarette smoking and certain chemical industry occupations and is one of the most prevalent forms of cancer in the general population. Furthermore, about half of those treated for bladder cancer will suffer a recurrence of the disease within five years of treatment. Thus, monitoring asymptomatic patients for recurrence of bladder lesions is particularly important. Providing efficient and inexpensive methods for the early detection and diagnosis of this disease could therefore provide significant public benefits.

Unfortunately, since the bladder cannot be examined by external viewing diagnosis of cancer or other ailments frequently does not occur until macroscopic hematuria (blood in the urine) or another observable symptom occurs. Methods such as cystoscopy and contrast urography are widely used for monitoring and diagnosing bladder cancer. However, cystoscopy involves an invasive examination of the bladder, is expensive to perform, and causes significant patient discomfort. Urine cytology, wherein cells collected from urine are examined for morphologic changes indicative of a disease state, is a non-invasive procedure but possesses insufficient sensitivity and accuracy for routine use.

Thus, it would be advantageous to have a more efficient, less invasive method for collecting cells from the internal organs of a subject. Such a method would reduce the cost of, and facilitate subject compliance with, detecting diseases in which cells from an internal organ are collected for performing diagnosis. Furthermore, such a method would facilitate the detection of disease states before macroscopic evidence of disease state became present and would facilitate inexpensive mass screening for diseases.

SUMMARY OF THE INVENTION

The present invention provides a method for collecting cells from an internal organ of a subject that is more efficient that traditional cytological methods and less invasive than methods of collection involving surgical procedures. Thus, the methods provided by the present invention reduce screening costs and facilitate subject compliance, thereby allowing for the detection of a disease state before macroscopic evidence of the disease state and inexpensive mass screening for a disease state.

In one embodiment, the present invention provides a method for collecting cells from an internal organ of a subject. First, energy from an external energy source is applied to the subject. The energy is effective to loosen cells from an internal cellular surface of an internal organ of the subject whereby at least some of the loosened cells are detached from the internal cellular surface of the internal organ. The detached cells are collected from the subject and can be screened for one or more disease states. In one embodiment, the disease state is characterized at least partly by telomerase expression. In another embodiment, the disease state is characterized partly by telomere length. In a related embodiment, the lengths of the telomeres of the collected cells are determined.

In one embodiment, the internal cellular surface of the internal organ of the subject is comprised of internal tissues chosen from the group consisting of bladder, kidney, colon, prostate, uterus, stomach, pancreas, and lung tissues. In a more specific embodiment, the internal cellular surface of the internal organ of the subject is comprised of bladder tissue. In a related embodiment, the cells detached from the internal cellular surface and subsequently collected are bladder epithelial cells. In still another embodiment, the bladder epithelial cells are deposited in the urine of the subject and subsequently isolated from the urine of the subject.

In one embodiment, the isolated bladder epithelial cells are analyzed for at least one disease state. In another embodiment, the disease state is characterized by telomerase expression. In a more specific embodiment, the disease state is cancer. In one such embodiment, telomerase expression is detected by a primer-based extension assay. In another such embodiment, telomerase expression is detected by an assay for the RNA component of telomerase. In still another such embodiment, telomerase expression is detected by an assay for the protein component of telomerase. In still another embodiment, the disease state of the bladder epithelial cells is characterized by changes in telomere length. In a yet more specific embodiment, the cancer is bladder cancer.

In a more specific embodiment, the external energy source is a vibrator and the applied energy is vibrational energy. In one such embodiment, the vibrator is applied to the subject for between about 1 minute to about 10 minutes. In a more specific embodiment, the vibrator is applied to the subject for between about 4 minutes to about 7 minutes. In a still more specific embodiment, the vibrator is applied to the subject for about 5 minutes.

In one particular embodiment, vibrational energy is applied to the bladder of a subject to dislodge bladder epithelial cells from the bladder. The subject's urine is collected and the bladder epithelial cells are collected from the urine. The bladder epithelial cells are analyzed for at least one disease state, and, more particularly, a disease state that is characterized by the presence of telomerase expression. In a more specific embodiment, the disease state is cancer. In a yet more specific embodiment, the cancer is bladder cancer. In one embodiment, telomerase expression is detected by an assay selected from the group consisting of a primer-based extension of a telomerase substrate, an assay for the RNA component of telomerase, an assay for the mRNA component(s) of telomerase, and an assay for the protein component(s) of telomerase.

These and other aspects and advantages of the present invention will become more apparent when the Description below is read in conjunction with the accompanying Drawings.

DETAILED DESCRIPTION OF SPECIFIC EMBODIMENTS

Figure 1:
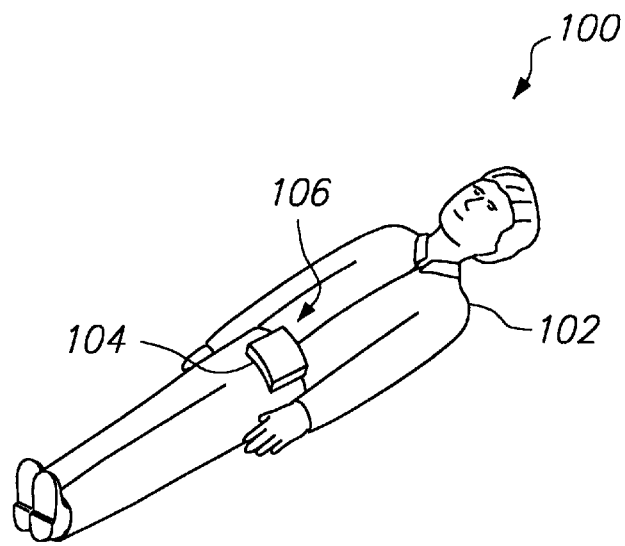
FIG. 1 is an illustration showing the application of external energy to a subject in accordance with one embodiment of the present invention.

The present invention provides less invasive and more efficient methods for collecting cells from internal organs of a subject than available using invasive, e.g., surgical, means. Such non-invasive methods for collecting cells will be appreciated to provide increased subject compliance with sample requests and decrease costs associated with disease diagnosis. Thus, the present invention will be seen to provide simple and inexpensive cell collection and diagnostic methods that are applicable to mass screening programs for diagnosing diseases such as cancer.

According to one embodiment of the present invention, energy from an external energy source is applied to a subject. The applied energy is effective to loosen cells from an internal cellular surface of an internal organ of the subject. More particularly, the applied energy is effective to detach at least some of the loosened cells from the internal cellular surface of the internal organ of the subject. The detached cells are then collected. The collected cells may be analyzed for the presence of disease.

The internal organ subjected to the applied external energy can be any biological structure internal to the body that performs a specific function and which includes an internal cellular surface from which the detached cells can be recovered from the body. Such organs include, without limitation, the lungs, kidneys, bladder, uterus, sinus, rectum, prostate, stomach, pancreas, oral cavities (including the throat), colon, and intestines. More particularly, the internal organs to which the energy is applied are those having internal cellular surfaces that comprise at least one passage leading from the interior of the body of the subject to the exterior of the subject's body. Such organs include the lungs, kidneys, bladder, uterus, sinus, rectum, prostrate, stomach, pancreas, oral cavities (including the throat), colon, and intestines. Although the "subjects" described herein will generally refer to human subjects, it will be appreciated that the methods of the present invention are also applicable to animals, and especially animals of veterinary interest such as dogs, cats, horses, sheep, pigs, and cows.

The external energy source can be any device capable of producing energy that is effective to loosen and detach at least some cells from an internal organ of a subject. For example, the energy source can be one capable of producing energy that is vibrational in nature, such as mechanical or ultrasonic vibrations, that are transmitted through the subject's tissues to the internal organ(s) of interest whereupon the vibrations loosen and detach cells from an internal cellular surface of the organ for collection. Examples of external energy sources suitable for use with the present invention are mechanical vibrators and ultrasound generators. Such devices can be purchased commercially.

The energy produced by the energy source can be directed to various tissues including those comprising the organ of interest simultaneously, or the energy source can be one capable of providing energy that is substantially focused on a specific internal organ. Localization can be achieved, for example, by attaching one or more external energy sources to the subject and choosing frequencies effective to cause maximal energy transmission to the organ of interest. Alternatively, various focusing devices can be employed.

Other methods of localization will be apparent to those of skill in the biophysical and medical arts. In addition, in some cases the energy will be directed to specific anatomical locations using information obtained from other diagnostic techniques effective to locate and identify malignancies, such as magnetic resonance imaging, ultrasound, radioisotopic studies, computerized axial tomography, X-rays, and the like.

Direct contact between the subject and the energy source is not strictly required so long as the energy reaching the organ of interest is effective to loosen and detach at least some cells from an interior surface of that organ for collection. For example, where ultrasound is the mode of energy transmission the subject can be immersed in a bath containing water or other fluid or solution that is effective for transmitting ultrasound energy to the organ of interest. However, direct contact between the energy source (e.g., a mechanical vibrator) and the subject can be employed. In addition, in some cases additional pressure can be placed on the external energy source to enhance the degree of contact between the energy source and the subject, using, for example, manual pressure, or a belt or strap or the like, that holds the energy source against the subject.

Operating parameters, such as the intensity of the applied energy, the duration of the application of the energy, and the form of the energy (e.g., mechanical vibration or ultrasound), will depend on various factors that are familiar to those of skill in the medical and biophysical arts. Such parameters include, without limitation, the subject' physical size, fat content and distribution, and the location of the organ of interest. The determination of these and other operational parameters can be made by those of skill in the medical and biophysical art using standard methods and materials.

For example, in those embodiments for which the applied energy is vibrational energy and the internal organ is the bladder, such as described in the Example provided below, the vibrational energy is applied to the subject for a duration of between about 1 minute and about 10 minutes. In a more particular embodiment, the vibrational energy is applied to the subject for a duration of between about 4 minutes and about 7 minutes. In still another embodiment, the vibrational energy is applied to the subject for a duration of about 5 minutes.

Without wishing to be bound by any particular theory of action, it is believed that the transmission of energy, particularly mechanical vibrational energy, to the cellular matrix defining an organ weakens the associative contacts between some of the cells comprising the organ causing at least some of those cells to loosen and detach from the internal cellular surfaces of the organ. These cells can include both malignant cells and proximal, non-malignant cells. Detached cells are completely separated from the internal cellular surface and are freed of the adhesive contacts with other cells that stabilize organ systems and thus can be collected, especially where those cells are from organs having internal surfaces that define a passage to the external surface of the subject, such as cells from the lung, bladder, kidneys, and rectum. In such cases, the detached cells can be recovered by the collection of bodily excretions, such as urine or sputum, by irrigation with an appropriate substance such as saline, or by swabbing or other means of physical collection.

Figure 2:
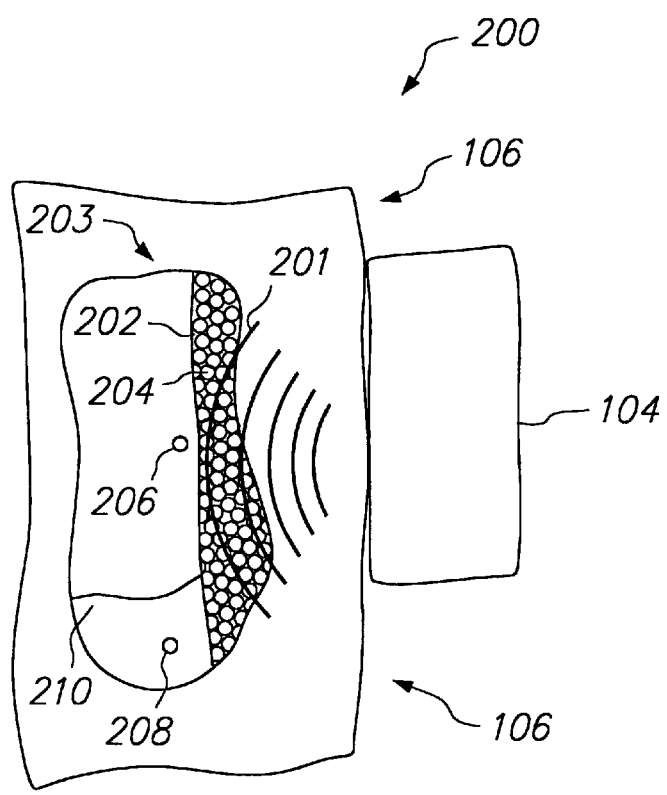
FIG. 2 is a cross-sectional view illustrating the loosening and detachment of bladder epithelial cells by the application of energy from an external energy source in accordance with one embodiment of the method of the present invention.

For example, in one embodiment, vibrational energy supplied by a vibrator loosens and detaches cells from the internal cellular surfaces of the bladder. Referring to FIG. 1 at 100, vibrational energy is transmitted to the bladder (not shown) of subject 102 from a vibrator 104 or other device capable of generating mechanical vibrations, such as a commercially available massaging unit, through the subject's lower abdominal region 106. Referring now to FIG. 2 at 200, mechanical vibrations 201 emitted by vibrator 104 loosen and detach cells from the inner wall 202 of bladder 203. The vibrational energy propagates through the tissues of the lower abdomen and bladder wall of subject 102 to the bladder epithelial cells 204 which comprise inner wall 202 of bladder 203. As described above, the transmitted vibrational energy is effective to loosen and dislodge bladder epithelial cells, such as cells 206 and 208 which are deposited into urine 210 retained in the bladder. Such deposited cells can be collected using standard methods when the subject voids his or her bladder. As described in detail in the Example below, the method of the present invention can increase the yield of bladder epithelial cells collected from the urine of a subject by about two-to eleven-fold as compared to cases where no such energy is applied.

In another aspect, the collected cells are analyzed for at least one disease state. The methods and materials used in the analysis of the cells will depend, at least in part, on the organ from which the cells are collected, and the disease state(s) for which the cells are being examined (e.g., bladder cancer). Such analysis can be performed using a variety of diagnostic methods well-known to one skilled in the medical and diagnostic arts. For example, where the collected cells are bladder epithelial cells, suitable diagnostic methods include, but are not limited to, the well-known techniques of: cystoscopy, cytology, flow cytometry, immunocytology, and contrast urography (Brendler, 1988, *J. Urol.* 139:342–343, Koss, 1989, *Cancer* 64:249–252, Huland, et al., 1991, *J. Urol.* 146:1631–1636). Similar methods for the analysis of cells collected from other internal organs will be apparent to those of skill in the medical and diagnostic arts.

In one embodiment, the disease state is characterized by the presence or level of telomerase expression. Telomerase is an ribonucleoprotein that synthesizes one strand of telomeric DNA using the enzyme's RNA component as a template (Blackburn, 1992, *Annu. Rev. Biochem.* 61:113–129). Telomerase expression has been detected in immortal cell lines and in various cancer lines, including bladder and lung cancers (Counter, et al., 1992, *EMBO* 11:1921–1929; Counter, et al., 1994, *Proc. Natl. Acad. Sci. USA* 91:2900–2940; Morin, 1989, *Cell* 59:512–529) and is currently one of the most specific and universal markers of cancer currently known (Kim, et al., 1994, *Science* 266:2011–2014; Muller, et al., 1996, *International J. Oticology* 19:1169–1173; Yoshida, et al., 1997, *Cancer* 79:362–369; Kinoshita, et al., 1997, *J. National Cancer Inst.* 89:724–730; Shay et al. 1997, *Eur. J. of Cancer* 33:787–791). Methods and reagents for diagnosing, prognosing, and treating diseases characterized by telomerase expression are described in U.S. Pat. No. 5,489,508 to West, et al. and U.S. Pat. No. 5,639,613 to Shay, et al; and U.S. patent application Ser. No. 08/060,952, filed May 13, 1993, and Ser. No. 08/255,774, filed Jun. 7, 1994. Each of the foregoing patent and non-patent references is incorporated herein by reference.

A number of highly sensitive methods for detecting telomerase have been described, see, e.g., PCT Application No. PCT/US94/12951, filed Nov. 10, 1994, and U.S. patent application Ser. No. 08/631,554, filed Apr. 12, 1996 now U.S. Pat. No. 5,863,726; Ser. No. 08/315,214, filed Sep. 28, 1994 now U.S. Pat. No. 5,629,154; and Ser. No. 08/482,132, filed Jun. 7, 1995 now U.S. Pat. No. 5,837,453, which include telomerase expression assays based on primer-based amplification techniques such as PCR. One such assay is the Telomeric Repeat Amplification Protocol ("TRAP") assay described by Kim, et al. in U.S. Pat. No. 5,629,154. This assay is available commercially from Oncor Inc. (USA) and Boehringer Mannheim GmbH (Germany). Other methods for determining the presence of telomerase expression include assays based on the RNA component of telomerase such as described in U.S. Pat. No. 5,583,016, to Villeponteau, et al., and in PCT Patent Application No. 93/23572. Still more assays for telomerase expression include assays for the mRNA and/or protein component(s) of telomerase such as described in co-pending U.S. patent application Ser. No. 08/724,643, filed Oct. 1, 1996, Ser. No. 08/844,419, filed Apr. 18, 1997, Ser. No. 08/846,017, filed Apr. 25, 1997, Ser. No. 08/851,843, filed May6, 1997, Ser. No. 08/854,050, filed May 9, 1997; and PCT Application Ser. No. PCT/US95/16531. Each of the foregoing is incorporated herein by reference.

In another embodiment, the disease state is characterized in part by telomere length. Chromosomes lose about 50–200 nucleotides of telomeric sequence per cell division (Harley, et al., 1990, *Nature* 345:458–460; Allsopp, et al., 1992, *Proc. Natl. Acad. Sci.* USA 89:10114–10118; Vaziri, et al., 1993, *Am. J. Human Genetics* 52:661–667; Watson, 1972, *Nature New Biology* 239:197–201). This cumulative loss of telomeric DNA has been implicated as a signal for replicative senescence and aging in normal somatic cells. (Allsopp, et al., 1992; Vaziri, et al., 1993; Hastie, et al., 1990, *Nature* 346:866–868; Lindsey, et al., 1991, *Mut. Res.* 256:45–48; Wright, et al., 1992, *Trends Genetics* 8:193–197). In contrast, most immortal cells, including many cancers, have telomeric sequences that do not diminish to biologically relevant lengths with cell division suggesting that telomere maintenance is associated with indefinite cell proliferation (Counter, et al., 1992; Counter, et al., 1994). Telomere length can be determined by TRF analysis which provides the composite lengths of all telomeres in a cell population (Harley, et al., 1990; Allsopp, et al., 1992; Vaziri, et al., 1993; Watson, 1972). Additional methods for determining telomere length and the use of telomere length for diagnosing disease are described in co-pending U.S. patent application Ser. No. 08/479,916, filed Jun. 7, 1995 now U.S. Pat. No. 5,741,677; and Ser. No. 08/660,442, filed Jun. 6, 1996 now U.S. Pat. No. 5,885,073.

EXAMPLE

The instant Example is offered solely to illustrate the features of the present invention and is not to be considered as limiting the scope of the present invention in any way.

A "Muscle Massager" vibrator (model # 199886) commercially available from Brookstone (Nashua, N.H.) was activated by turning the vibration control to the "Hi" setting. The vibration unit was placed into a "SoftTunes" protective carrier manufactured by Bollinger (Irving, Tex.). The vibrator was strapped onto the lower abdomen of the subject and the subject's hands were rested on the top of the device to apply a slight additional pressure to further secure the device against the subject's lower abdomen.

After about 5 minutes of vibration, the vibrator was removed and about 40 ml of freshly voided urine was collected from the subject and placed in a 50 ml centrifuge tube. The urine sample was centrifuged at about 500 g for about 15 minutes to pellet the cells. The supernatant was discarded and the pellet was re-suspended in about 20 ml of calcium-and magnesium-free phosphate-buffered saline (PBS, 10 mM $K_2PO_4$, 150 mM NaCl, pH 7.5). The cell suspension was then centrifuged at about 500 g for about fifteen minutes and the supernatant discarded. The cell pellet was re-suspended in about 1 ml of PBS and was transferred to a 1.5 ml centrifuge tube. The collected bladder epithelial cells were counted using standard techniques.

TABLE 1

| Individual | Number of Cells Collected in Urine Without External Stimulation | Number of Cells Collected in Urine Following the Method of the Invention | Relative Collection Efficiency |
|---|---|---|---|
| 1 | 50 | 400 | 8:1 |
| 2 | 750 | 3,200 | 4.3:1 |
| 3 | 350 | 4,000 | 11.4:1 |
| 4 | 14,550 | 26,850 | 1.8:1 |

Table 1 demonstrates the effectiveness of the present invention for increasing the number of bladder epithelial cells collected in the urine of four individual patients using the above described method. As shown by the data, the number of bladder epithelial cells collected using the method of the invention increase from about 1.8-to about 11.4-fold as compared with the number of bladder epithelial cells collected with no external stimulation.

CONCLUSION

Thus, it will be seen that the present invention provides a relatively non-invasive and efficient method for collecting cells from the internal organs of a subject. Such methods provide an alternative to invasive procedures, thereby improving subject compliance with, and reducing the cost of, screening techniques requiring the collection of cells from the subject's internal organs. In one embodiment, this aspect is demonstrated by the substantially non-invasive method for collecting and analyzing bladder epithelial cells from urine provided by the present invention. The greater efficiencies provided by the instant invention will also be seen to provide improved methods for screening large numbers of individuals for a disease state.

While the invention has been described in some detail to facilitate understanding, it will be apparent that certain changes and modifications may be practiced within the scope of the appended claims. For example, those of skill in the biophysical and medical arts will recognize that different type of external energy sources other than vibrators and/or ultrasound generators can be used to create the energy used to loosen and dislodge cells. Also, it will be appreciated that cells can be collected using many different procedures. Moreover, those of skill in the medical and biophysical arts will recognized that the methods described herein can be applied to many other internal organs in addition to those exemplified herein.

What is claimed is:

1. A method for collecting cells from the bladder of a subject comprising the steps of:
   a. applying vibrational energy from an external energy source to said subject, said applied energy being effective to loosen cells from an internal cellular surface of the bladder of said subject such that at least a portion of said loosened cells are detached from said internal cellular surface; and
   b. collecting said detached cells from said subject.

2. The method of claim 1, further comprising analyzing said collected cells for at least one disease state.

3. The method of claim 2, wherein said disease state is characterized at least in part by telomerase expression.

4. The method of claim 3, wherein said step of analyzing said collected cells comprises determining the presence of telomerase expression.

5. The method of claim 2, wherein said disease state is characterized at least in part by telomere length.

6. The method of claim 5, wherein said step of analyzing said collected cells comprises determining the lengths of telomeres in said cells.

7. The method of claim 1, wherein said cells are bladder epithelial cells.

8. The method of claim 7, wherein said bladder epithelial cells are deposited in the urine of said patient and said method further comprises the step of isolating said bladder epithelial cells from said urine.

9. The method of claim 8 further comprising the step of analyzing said bladder epithelial cells for at least one disease state.

10. The method claim 9, wherein said disease state is characterized by telomerase expression.

11. The method of claim 10, wherein said at least one disease state is cancer.

12. The method of claim 11, wherein said cancer is bladder cancer.

13. The method of claim 11, wherein said telomerase expression is detected by a primer-based extension assay for telomerase.

14. The method of claim 11, wherein said telomerase expression is detected by an assay for the RNA component of telomerase.

15. The method of claim 11, wherein said telomerase expression is detected by an assay for the protein component of telomerase.

16. The method of claim 9, wherein said disease states are characterized by changes in telomere length.

17. The method of claim 16, wherein said at least one disease state is cancer.

18. The method of claim 17, wherein said cancer is bladder cancer.

19. The method of claim 18, wherein said vibrational external energy source is a vibrator.

20. The method of claim 19, wherein said vibrator is applied to said subject for between about 1 minute to about 10 minutes.

21. The method of claims 20, wherein said vibrator is applied to said subject for between about 4 minutes to about 7 minutes.

22. The method of claim 21 wherein said vibrator is applied to said subject for about 5 minutes.

23. A method for collecting bladder epithelial cells from a subject comprising the steps of:
   a. applying vibrational energy to said subject using a vibrator, said vibrational energy being effective to loosen bladder epithelial cells from an interior wall of the bladder of said subject such that said loosened bladder epithelial cells from said interior wall of said bladder are deposited in the urine of said subject;
   b. collecting said urine from said subject; and
   c. isolating said bladder epithelial cells from said urine of said subject.

24. The method of claim 23, further comprising analyzing said bladder epithelial cells from said subject for at least one disease state.

25. The method of claim 18, wherein said vibrational external energy source is an ultrasound generator.

26. The method of claim 23, wherein said vibrator is applied to said subject for between about 1 minute to about 10 minutes.

27. The method of claim 26, wherein said vibrator is applied to said subject for between about 4 minutes to about 7 minutes.

28. The method of claim 27 wherein said vibrator is applied to said subject for about 5 minutes.

29. The method of claim 24, wherein said disease state is characterized by telomerase expression.

30. The method of claim 29, wherein said disease state is cancer.

31. The method claim 30, wherein said cancer is bladder cancer.

32. The method of claim 31, wherein said telomerase expression is detected by an assay selected from the group consisting of primer-based extension assays for telomerase, an assay for the RNA component of telomerase, an assay for the mRNA component(s) of telomerase, and an assay for the protein component(s) of telomerase.

* * * * *